(12) United States Patent
Pegan et al.

(10) Patent No.: US 9,394,254 B2
(45) Date of Patent: Jul. 19, 2016

(54) ANTIBIOTIC AND ANTI-PARASITIC AGENTS THAT MODULATE CLASS II FRUCTOSE 1,6-BISPHOSPHATE ALDOLASE

(71) Applicants: Colorado Seminary, Denver, CO (US); Regis University, Denver, CO (US)

(72) Inventors: Scott Dusan Pegan, Denver, CO (US); Kateri Ahrendt, Boulder, CO (US); Glenn C. Capodagli, Denver, CO (US); Bryan Cowen, Denver, CO (US)

(73) Assignee: The University of Denver and Regis University, Denver, CO (US)

( * ) Notice: Subject to any disclaimer, the term of this patent is extended or adjusted under 35 U.S.C. 154(b) by 0 days.

(21) Appl. No.: 14/273,411

(22) Filed: May 8, 2014

(65) Prior Publication Data
US 2014/0336221 A1    Nov. 13, 2014

Related U.S. Application Data

(60) Provisional application No. 61/821,184, filed on May 8, 2013.

(51) Int. Cl.
| | | |
|---|---|---|
| *C07D 221/02* | (2006.01) | |
| *C07D 215/48* | (2006.01) | |
| *A01N 43/42* | (2006.01) | |
| *C07D 401/04* | (2006.01) | |
| *C07D 413/04* | (2006.01) | |
| *C07D 417/04* | (2006.01) | |
| *C12Q 1/527* | (2006.01) | |

(52) U.S. Cl.
CPC .............. *C07D 215/48* (2013.01); *A01N 43/42* (2013.01); *C07D 401/04* (2013.01); *C07D 413/04* (2013.01); *C07D 417/04* (2013.01); *C12Q 1/527* (2013.01); *G01N 2333/988* (2013.01); *G01N 2500/04* (2013.01)

(58) Field of Classification Search
CPC .................................................... C07D 215/48
USPC ......................................................... 546/183
See application file for complete search history.

(56) References Cited

U.S. PATENT DOCUMENTS

| 889,704 | A | * | 6/1908 | Blake | ..................... | F16C 23/084 |
|---|---|---|---|---|---|---|
| | | | | | | 384/495 |
| 8,138,181 | B2 | * | 3/2012 | Allen | ................... | C07D 47/104 |
| | | | | | | 514/230.5 |
| 2004/0006040 | A1 | | 1/2004 | Schechter | | |
| 2004/0057963 | A1 | | 3/2004 | Andersen et al. | | |
| 2004/0101874 | A1 | | 5/2004 | Ghosh et al. | | |
| 2008/0027044 | A1 | | 1/2008 | Lewis et al. | | |
| 2011/0184013 | A1 | * | 7/2011 | Allen | ................... | C07D 487/04 |
| | | | | | | 514/300 |
| 2014/0050761 | A1 | | 2/2014 | Bergeron et al. | | |

FOREIGN PATENT DOCUMENTS

| EP | 336356 | * | 10/1989 | ........... C07D 209/42 |
|---|---|---|---|---|
| JP | 57059938. | * | 9/1980 | ............... C08L 23/00 |
| KR | 2008105577 | * | 12/2008 | ........... C07D 209/42 |
| WO | WO 2010022076 | * | 2/2010 | ........... C07D 471/04 |
| WO | 2014/182954 A1 | | 11/2014 | |

OTHER PUBLICATIONS

Corsini et al. Canadian Journal of Chemistry (1969), 47(24), 4655-9.*
Puckett et al. PLOS Pathogens, May 2014 | vol. 10 | Issue 5 | e1004144.*
International Search Report and Written Opinion for PCT/US2014/37375, mailed on May 8, 2014, 12 pages.
Born et al., "Tuberculostatic Effect of 8-Hydroxyquinoline and Its Derivatives," Orvosi Hetilap: Hungarian Medical Journal 93(13): 400-402 (1952).
Connor et al., "Structural and Functional Characterization of *Mycobacterium tuberculosis* Triosephosphate Isomerase," Acta Crystollograhica, Section D, Biological Crystallography 67(12): 1017-1022 (2011).
Darby et al., "Killing of Non-Replicating *Mycobacterium tuberculosis* by 8-Hydroxyquinoline," Journal of Antimicrobial Chemotherapy 65: 1424-1427 (2010).
De La Paz Santangelo et al., "Glycolytic and Non-Glycolytic Functions of *Mycobacterium tuberculosis* Fructose-1,6-Bisphosphate Aldolase, an Essential Enzyme Produced by Replicating and Non-Replicating Bacilli," The Journal of Biological Chemistry 286(46): 40219-40231 (2011).
Enquist et al., "Derivatives of 8-Hydroxyquinoline—Antibacterial Agents that Target Intra- and Extracellular Gram-Negative Pathogens," Bioorganic & Medicinal Chemistry Letters 22(10): 3550-3553 (2012).
Fonvielle et al., "New Highly Selective Inhibitors of Class II Fructose-1,6-Biphosphate Adolases," Bioorganic & Medicinal Chemistry Letters 14(11): 2923-2626 (2004).
Fonvielle et al., "Synthesis and Biochemical Evaivation of Selective Inhibitors of Class II Fructose Biphosphate Adolases: Towards New Synthetic Antibiotics," Chemistry: A European Journal 14(28): 8521-8529 (2008).
Froude et al., "Antibodies for Biodefense," mAbs 3(6): 517-527 (2011).
Fujikawa et al., "Studies on Chemotherapeutics for Mycobacterium Tuberculosis 18. Synthesis and Antibacterial Activity on Mycobacterium Tuberculosis of Formyl-8-Hydroxyquinoline Derivatives," Yakugaku Zasshi: Journal of the Pharmaceutical Society of Japan 87(7): 844-849 (1967).

(Continued)

*Primary Examiner* — Nizal Chandrakumar
(74) *Attorney, Agent, or Firm* — Kilpatrick Townsend & Stockton LLP

(57) ABSTRACT

This invention provides a family of compounds that inhibit Class II fructose 1,6-bisphosphate aldolase (FBA), which is implicated in the pathogenic activity of a broad range of bacterial and parasitic agents. The compounds were identified by empirical testing, and provide a basis for further derivatization and optimization of 8-hydroxyquinoline-2-carboxylic acid and related compounds. Crystal structure shows that the compounds don't bind directly to the catalytic site of the enzyme, and so are not defined simply as substrate analogs. Instead, they create a pocket by induced fit, resulting a powerful and specific inhibitory effect on FBA activity.

11 Claims, 9 Drawing Sheets

(56) References Cited

OTHER PUBLICATIONS

Gavalda et al., "N-Sulfonyl Hydroxamate Derivatives as Inhibitors of Class II Fructose-1,6-Diphosphate Adolase," Bioorganic & Medicinal Chemistry Letters 15: 5375-5377 (2005).

Juhasz et al., "The In Vitro Effect of 8-Hydroxyquinoline Derivatives on Strains of Mycobacterium Tuberculosis," Biochemical Pharmacology 12: 235-239 (1964).

Labbe et al., "Development of Metal-Chelating Inhibitors for the Class II Fructose 1,6-Biphosphate (FBP) Adolase," Journal of Inorganic Biochemistry 112: 49-58.

Li et al., "Rational Design, Synthesis and Evaluation of First Generation Inhibitors of the Giardia Larnblia Fructose-1,6-Biphosphate Adolase," Journal of Inorganic Biochemistry 105(4): 509-517 (2011).

Lipinski et al., "Experimental and Computational Approaches to Estimate Solubility and Permeability in Drug Discovery and Development Settings," Advanced Drug Delivery Reviews 46(1-3): 3-26 (2001).

Manske, "The Chemistry of Quinolines," Chemical Reviews 30(1): 113-144 (1942).

Pegan et al., "Active Site Loop Dynamics of a Class IIa Fructose 1:6-Biphosphate Adolase from Mycobacterium Tuberculosis," Biochemistry 52(5): 912-925 (2013).

Pegan et al., "Structural Basis for Catalysis of a Tetrameric Class IIa Fructose 1,6-Biphosphate Adolase from Mycobacterium Tuberculosis," Journal of Molecular Biology 386(4): 1038-1053 (2009).

Perez et al., "Carbapenem-Resistant Enterobacteriaceae: A Menace to Our Most Vulnerable Patients," Cleveland Clinical Journal of Medicine 80(4): 225-233 (2013).

Rees et al., "Fragment-Based Lead Discovery," Nature Reviews Drug Discovery 3(8): 660-672 (2004).

Rodaki et al., "Effects of Depleting the Essential Central Metabolic Enzyme Fructose-1,6-Biphosphate Adolase on the Growth and Viability of Candida Albicans: Implications for Antifungal Drug Target Discovery," Eukarotic Cell 5(8): 1371-1377 (2003).

Scheffler et al., "Antimicrobials, Drug Discovery, and Genome Mining," Applied Microbiology and Biotechnolooy 97(3): 969-978 (2013).

Shrader et al., "Synthesis of a Novel Hexadentate Chelating Agent based on 8-Hydroxyquinoline," Tetrahedron Letters 29(12): 1351-1354 (1988).

Sobke et al., "The Urinary Antibiotic 5-Nitro-8-Hydroxyquinoiine (Nitroxoline) Reduces the Formation and Induces the Dispersal of Pseudomonas Aeruginosa Biofilms by Chelation of Iron and Zinc," Antimicrobial Agents and Chemotherapy 56(11): 6021-6025 (2012).

Veber et al., "Molecular Properties that influence Oral Bioavailability of Drug Candidates," Journal of Medicinal Chemistry 45(12): 2615-2623 (2002).

* cited by examiner

FIG. 2
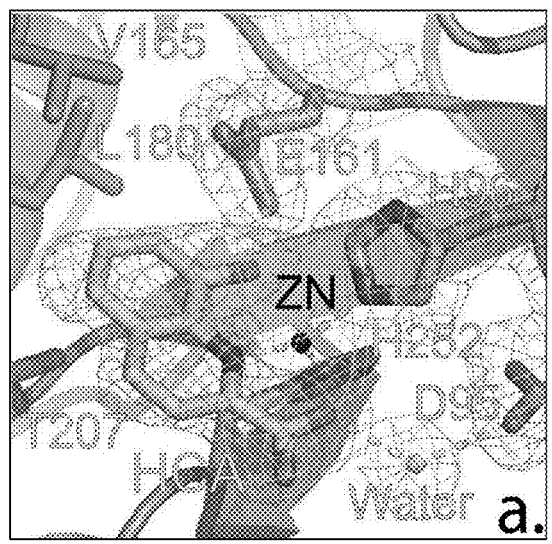
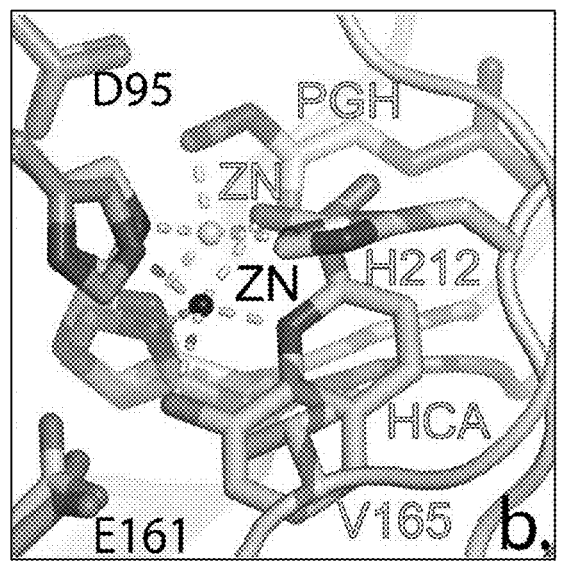
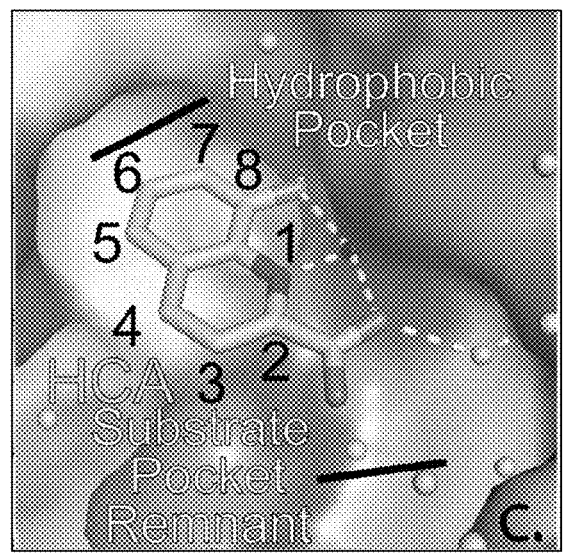

```
           Substrate pocket  Hydrophobic pocket
              * *          *    *         *
    94 TDHC 160 IELGVV 180 VT  M. tuber.
   109 TDHC 174 IELGCT 196 VT  Y. pestis
    84 LDHG 136 AELGTV 154 IYA S. aureus
    84 LDHG 136 AELGTV 154 IYA B. athrac
    83 LDHG 135 AELGT  153 IYA K. pneum
```
FIG. 3
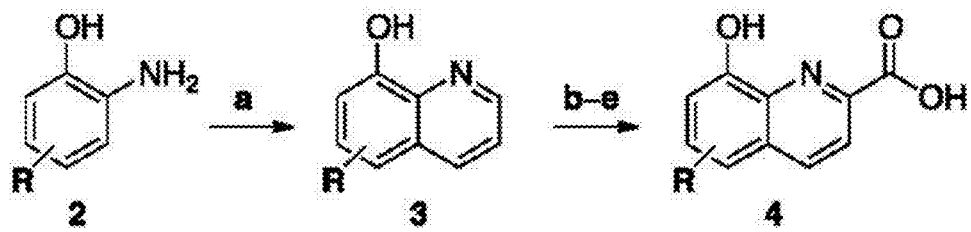
Reagents: (a) glycerol, PhNO$_2$, 140 °C; (b) m-CPBA; (c) (CH$_3$O)$_2$SO$_2$; (d) NaCN; (e) NaOH
FIG. 4A
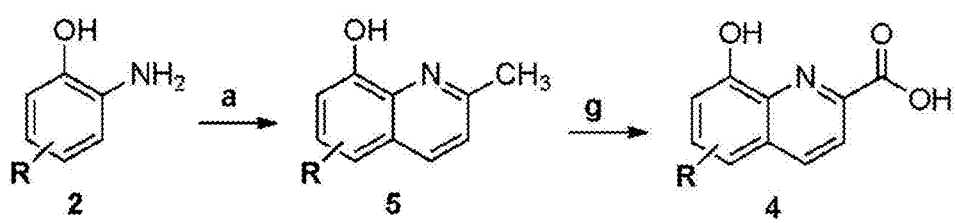
Reagents: (f) crotonaldehyde, HCl/toluene, reflux; (g) SeO$_2$, pyridine, 90 °C
FIG. 4B

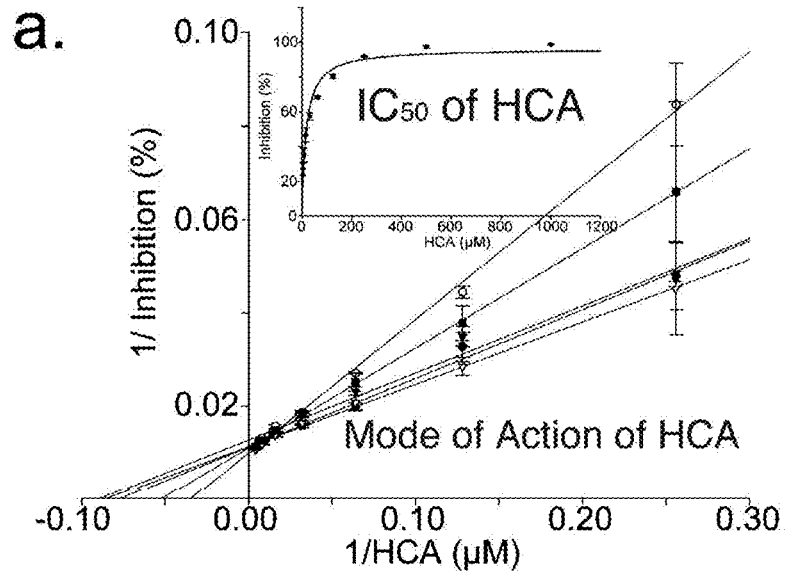
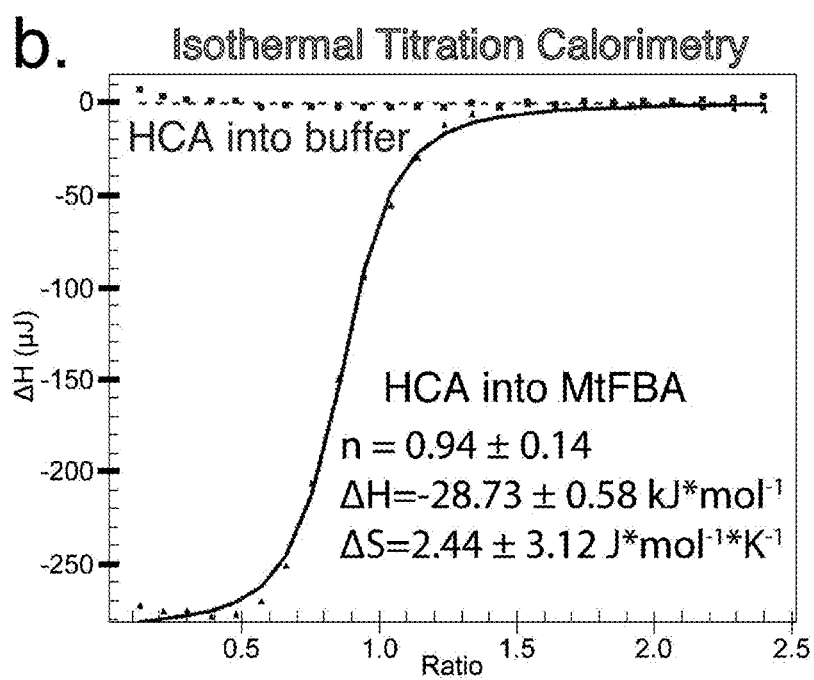
FIG. 6

FIG. 7A

Homo sapiens gene for fructose bisphosphate aldolase
GenBank: X07292.1

MPHSYPALSAEQKKELSDIALRIVAPGKGILAADESVGSMAKRL
SQIGVENTEENRRLYRQVLFSADDRVKKCIGGVIFFHETLYQKDDNGVPFVRTIQDKG
IVVGIKVDKGVVPLAGTDGETTTQGLDGLSERCAQYKKDGADFAKWRCVLKISERTPS
ALAILENANVLARYASICQQNGIVPIVEPEILPDGDHDLKRCQYVTEKVLAAVYKALS
DHHVYLEGTLLKPNMVTPGHACPIKYTPEEIAMATVTALRRTVPPAVPGVTFLSGGQS
EEEASFNLNAINRCPLPRPWALTFSYGRALQASAVNAWRGQRDNAGAATEEFIKRAEV
NGLAAQGKYEGSGEDGGAAAQSLYIANHAY

FIG. 7B

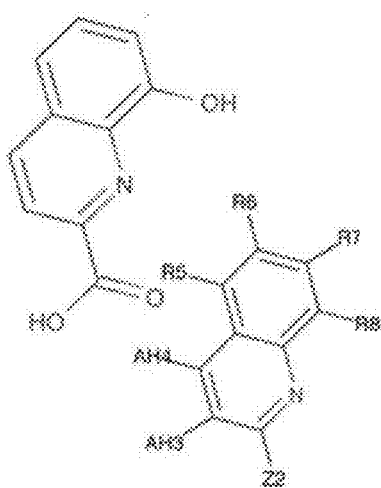
*FIG. 8A*
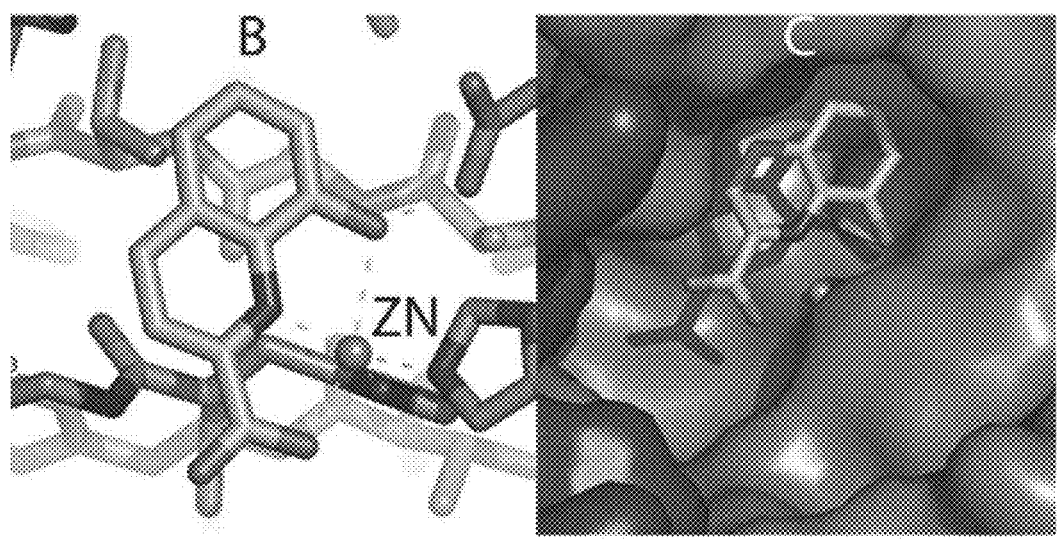
*FIG. 8B*  *FIG. 8C*

ANTIBIOTIC AND ANTI-PARASITIC AGENTS THAT MODULATE CLASS II FRUCTOSE 1,6-BISPHOSPHATE ALDOLASE

RELATED APPLICATION

This application claims the priority benefit of U.S. provisional patent application 61/821,184, filed May 8, 2013. The priority application is hereby incorporated herein by reference for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 92154-907655—ST25.TXT, created Jun. 6, 2014, 17,149 bytes, machine format IBM-PC, MS-Windows operating system, is hereby incorporated by reference.

FIELD OF THE INVENTION

This application relates to the field of treatment and prevention of bacterial and parasitic conditions. The compounds of the invention inhibit enzyme activity of Class II fructose 1,6-bisphosphatase aldolase of the microorganism targeted for therapy.

BACKGROUND

*Mycobacterium tuberculosis*, the causative agent for Tuberculosis (TB), currently infects one third of the world's population in its latent form. In 2011 alone, 8.7 million new cases of TB were detected and 1.4 million deaths were attributed to infection by this pathogenic bacteria. World Health Organization, *Global tuberculosis Report* 2012. For the U.S. in particular, the danger of TB has been significantly risen recently with the by the rapid increasing prevalence of TB cases amongst HIV infected patients. World Health Organization, UNAIDS, and UNICEF, *Global HIV/AIDS response: epidemic update and health sector progress towards universal access: Progress Report* 2011.

Current treatment for TB, Directly Observed Therapy, Short Course (DOTS), involves the administration of a four-drug cocktail over a two month time span with continuous two-drug treatments for an additional 2-4 months. *Implementing the Stop TB Strategy: a handbook for national tuberculosis*, 2008, World Health Organization: Geneva, Switzerland. p. 1-198. Despite increasing global efforts to eradicate TB, the estimated rate of curing TB cases has actually declined in last couple of years. Part of this decline has been an upsurge of cases involving multidrug resistant TB strains, MDR-TB and XDR-TB, as well as the increased difficulty of patients complying the lengthy DOTS regiment.

Unfortunately, *M. tuberculosis* is not the only pathogenic bacterium that has become resistant to current antibiotics. Increasing incidents of other drug resistant bacterium such as Methicillin-resistant *Staphylococcus aureus* (MRSA) and Carbapenem-resistant Enterobacteriaceae (CRE) are also on the rise. Perez F. et al., Cleve. Clin J Med, 2013. 80(4):225-33; Scheffler, R. J, et al., Appl Microbiol Biotechnol, 2013. 97(3): 969-78. Additionally, the threat of drug-resistant weaponized bacterium such as *Bacillus anthracia* and *Yersinia pestis* still persists. Froude, J. W, et al., *Antibodies for biodefense*. MAbs, 2011. 3(6):517-27.

With the global decreasing effectiveness of current therapeutics against TB, increasing prevalence the multi-drug resistant strains MDR-TB and XDR-TB as well as other pathogenic bacterium, there is a strong need for development of antibiotics targeting novel pharmacological targets within pathogenic bacterium such as *M. tuberculosis*.

SUMMARY OF THE INVENTION

This invention provides antibiotics and anti-parasitic agents that inhibits Class II fructose 1,6-bisphosphate aldolase (FBA). Typically, they inhibit Class II FBA of the microorganism targeted for treatment, or a homolog thereof, but not Class I FBAs such as may be expressed in human or mammalian subjects.

Model compounds have the structure shown in Formula (I).

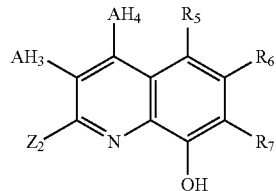

Formula (I)

In some embodiments of the invention, $R_7$=H, alkyl, alkenyl, alkynyl, F, Cl, Br, $CF_3$, or OH; $R_6$=H, alkyl, alkenyl, alkynyl, F, Cl, Br, or $CF_3$; $R_5$=H, alkyl, alkenyl, alkynyl, F, Cl, Br, $CF_3$, or OH; $AH_4$=H, alkyl, alkenyl, alkynyl, aryl, F, Cl, Br, $CF_3$, or OH; $AH_3$=H, alkyl, alkenyl, alkynyl, aryl, F, Cl, Br, $CF_3$, or OH; and $Z_2$=$CO_2H$, $CO_2R$, $CONH_2$, CONHR, aryl, or heteroaryl.

The compounds of the invention can be selected to have antibiotic and/or anti-parasitic activity for a broad range of pathogenic agents or for certain pathogenic agents in particular. The compounds in inhibits growth or replication of organisms such as *M. tuberculosis*, or any of the other organisms referred to in this disclosure. Model compounds may be selected as having any one or more of the properties explained in this disclosure in any combination. For example, a model compound may bind to a Class II fructose 1,6 bisphosphate aldolase (FBA) such as those having an amino acid sequence according to any one or more of SEQ. ID NOs:1 to 5. FBA binding of the compound may have a dissociation constant (Kd) of less than about 100 μM, 10 μM, 1 μM, or 0.1 μM. The compound may substantially inhibit enzymatic activity of a Class II fructose 1,6 bisphosphate aldolase (FBA) such as SEQ. ID NOs:1 to 5, with minimal inhibition of a Class II or mammalian FBA such as SEQ. ID NO:6. Some model compounds of this invention induce their own binding site in the flexible Z loop structure of Class II FBA.

Reference to any drug or active agent in this disclosure includes any and all isomers, stereoisomers, pharmaceutically compatible salts, solvates, and pharmaceutical compositions thereof that retain at least some of the physiological or chemotherapeutic effects of the drug itself, unless such isomers, salts, solvates, and/or compositions are explicitly excluded. Any such compound may be used as an alternative to the drug itself to improve efficacy, tolerability, delivery, or pharmacokinetics, or simply by choice within the good judgment of the manufacturer, distributor, pharmacist, clinician, or end user.

Other aspects of the invention are pharmaceutical compositions, disinfectants, and soaps that comprise one or more compounds of this invention. They may be used in the treatment of infection, in the disinfecting of surfaces and equipment, and in the manufacture of medicaments. Another aspect of the invention is a method of killing or modulating growth of a bacterium or parasite, comprising contacting the bacterium or parasite with a compound or composition as described herein. Another aspect of the invention is a method for treatment of an infection by any bacterial or parasitic agent, such as an agent which expresses Class II fructose 1,6-bisphosphate aldolase (FBA), and which rely on FBA activity for viability, growth, or metabolism.

Another aspect of the invention is a screening method for identifying compounds suitable for use as antibiotics or anti-parasitic agents. The method comprises measuring enzymatic activity of a Class II fructose 1,6-bisphosphate aldolase (FBA) in the presence and absence of the compound, and determining whether the compound inhibits the enzymatic activity of the FBA. The method may further comprise measuring enzymatic activity of a Class I FBA, determining whether the compound inhibits growth or metabolism of a bacterium or a parasite, and/or determining the crystal structure of an FBA to which the compound has bound.

This invention provides additional compounds and derivatives of 8-hydroxyquinoline-2-carboxylic acid (HCA) that are identified as having antibiotic and/or anti-parasitic activity and/or FBA inhibitory capacity according to the methods of this invention.

Other aspects of the invention will be apparent from the description that follows.

DRAWINGS

FIG. 1 is a schematic depiction of the role of Fructose-bisphosphate aldolase (FBA) in the gluconeogenesis and glycolysis pathways in *Mycobacterium tuberculosis* (MtFBA).

FIG. 2 shows how compounds and derivatives of 8-hydroxyquinoline-2-carboxylic acid (HCA) having antibiotic and/or anti-parasitic activity according to this invention bind in the X-ray crystallographic structure of MtFBA. In FIG. 2A HCA (the bicyclic compound) is shown bound to neighboring amino acid residues in MtFBA. FIG. 2B is another view with MtFBA-PGH structure overlaid. Zn(II) and residues in frame belonging to the MtFBA-PGH structure are rendered in grey. FIG. 2C shows HCA binding cavity on MtFBA.

FIG. 3 shows similarity of key residues of FBA from different pathogens around about the HCA binding pocket. Due to the conserved nature of Class II 1,6-bisphosphate aldolases, HCA can be used to treat and manage a wide range of other pathogenic bacteria and parasitic eukaryotes. Sequence legend: TDHC (SEQ ID NO:1, residues 94-97); IEIGVV (SEQ ID NO:1, residues 160-165); TDHC (SEQ ID NO:2, residues 109-112); IELGCT (SEQ ID NO:2, residues 174-179); LDHG (SEQ ID NO:3, residues 84-87); AELGTV (SEQ ID NO:3, residues 136-141); LDHG (SEQ ID NO:4, residue 84-87); AELGTV (SEQ ID NO:4, residues 136-141); LDHG (SEQ ID NO:5, residues 83-86); AELGTI (SEQ ID NO:5, residues 135-140).

FIGS. 4A and 4B illustrate chemical synthesis of the HCA compounds and derivatives of this invention.

FIG. 5 provides data from the calorimetric titration of HCA. Left-side panels show 5 mM of the compound designated as Regis 5 titrated into 700 µM of MtFBA demonstrating a dissociation constant Kd=6.94±0.97 µM. Right-side panels show the same compound titrated into MtFBA buffer in the presence of 200 µM $ZnCl_2$, showing no appreciable binding. Top graphs represent raw heat data and bottom graphs are integrated heat peaks gained at 25° C.

FIG. 6 illustrate MtFBA inhibitor properties of HCA. FIG. 6A is a Lineweaver-Burk plot of the kinetics of inhibition of MtFBA by 8-hydroxyquinoline-2-carboxylic acid against MtFBA for varying concentrations of FBP. The inset is a Michaelis-Menten plot of inhibition of MtFBA. FIG. 6B is isothermal Titration calorimetry (ITC) of HCA binding to MtFBA.

FIG. 7A is the amino acid sequence alignment of Class II FBAs from pathogenic bacteria. FBAs are from the H37RV strain of *M. tuberculosis* (SEQ. ID NO:1), *Yersinia pesti* (SEQ. ID NO:2), *Staphylococcus aureus* (SEQ. ID NO:3), *Bacillus anthracia* (SEQ. ID NO:4), and *Klebsiella pneumonia* (SEQ. ID NO:5). Asterisks denote residues involved in hydrophobic interactions as well as hydrogen bonds formed between MtFBA and HCA. FIG. 7B is the amino acid sequence of human Class I FBA (SEQ. ID NO:6).

FIG. 8A shows the general chemical structure of 8-hydroxyquinoline-2-carboxylic acid and its chemical scaffold. FIG. 8B is the X-ray crystal structure of 8-hydroxyquinoline-2-carboxylic acid bound to MtFBA. FIG. 8C is a surface rendering that shows 8-hydroxyquinoline-2-carboxylic acid bound to MtFBA binding cavity.

DETAILED DESCRIPTION

Figure 1:
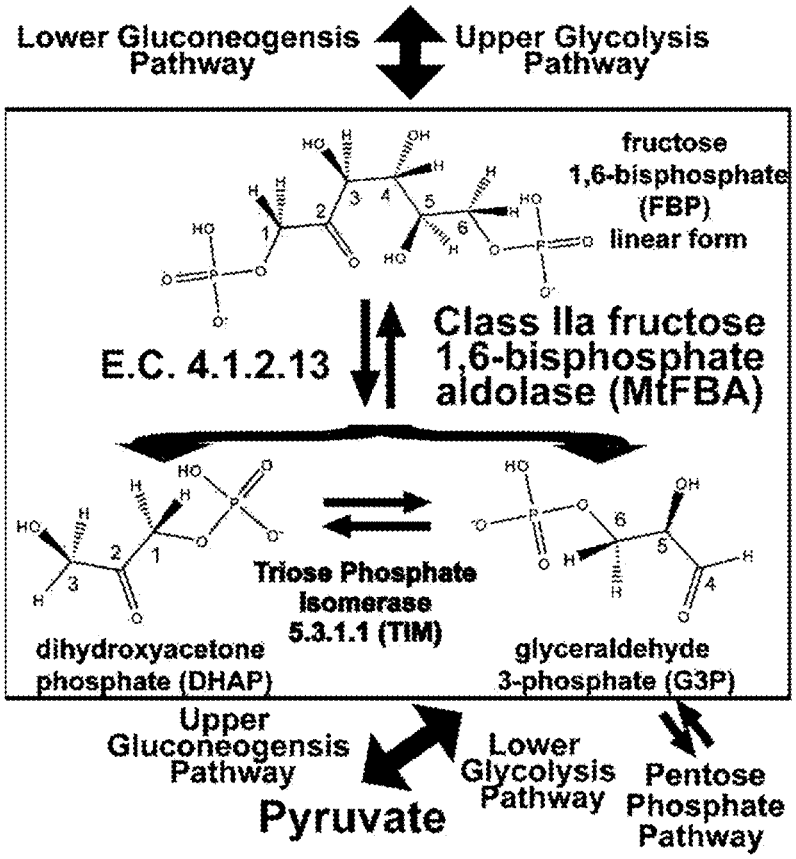

This invention provides a family of compounds that inhibit Class II fructose 1,6-bisphosphate aldolase (FBA), which is implicated in the pathogenic activity of a broad range of bacterial and parasitic agents. The compounds were identified by empirical testing, and provide a basis for further derivatization and optimization of 8-hydroxyquinoline-2-carboxylic acid (HCA) and related compounds. Crystal structure shows that the compounds don't bind directly to the catalytic site of the enzyme, and so are not defined simply as substrate analogs. Instead, they create a pocket by induced fit, resulting a powerful and specific inhibitory effect.

Fructose 1,6-Bisphosphate Aldolase (FBA) Activity in Pathogenic Bacteria

A molecular target for treating tuberculosis (TB) and other pathogenic bacteria is Class II fructose 1,6-bisphosphate aldolase (FBA). Class II FBAs are critical for bacterial, fungal and protozoan glycolytic/gluconeogenesis pathways due to their ability to catalyze the reversible enol condensation of dihydroxyacetone phosphate (DHAP) and glyceraldehyde 3-phosphate (G3P) to fructose 1,6-bisphosphate (FBP). Importantly, humans lack this type of aldolase, which make Class II FBA a promising therapeutic target. Small drug-like molecules that inhibit Class II FBA represent a new class of compounds structurally divergent from existing antibiotics, for which bacterial resistance has evolved.

Fructose-bisphosphate aldolase (FBA) (EC 4.1.2.13) is an enzyme catalyzing a reversible reaction that splits the aldol, fructose 1,6-bisphosphate, into the triose phosphates dihydroxyacetone phosphate (DHAP) and glyceraldehyde 3-phosphate (GAP). There are two families of aldolases.

Class II FBA differ from Class I FBA in that instead of forming a Schiff base intermediate using an ε-amino group of a lysine side chain, Class II FBAs utilize Zn(II) to stabilize a proposed hydroxyenolate intermediate (HEI) in the reversible cleavage of fructose 1,6-bisphosphate, forming DHAP and GAP. Class II FBA play an essential role in pathogenic bacteria, and accordingly are potential antibacterial targets. Although structural studies of Class II FBAs from *Mycobacterium tuberculosis* (MtFBA), other bacteria, and protozoa have been reported, the structure of the active site loop responsible for catalyzing the protonation-deprotonation steps of the reaction for Class II FBAs was not previously identified.

We have used the potent Class II FBA inhibitor phosphoglycolohydroxamate (PGH) as a mimic of the HEI- and DHAP-bound form of the enzyme and determined the X-ray structure of the MtFBA-PGH complex to 1.58 Å. We observed well-defined electron density for the previously elusive active site loop of MtFBA trapped in a catalytically competent orientation. Utilization of this structural information and site-directed mutagenesis and kinetic studies conducted on a series of residues within the active site loop revealed that E169 facilitates a water-mediated deprotonation-protonation step of the MtFBA reaction mechanism. Solvent isotope effects on MtFBA and catalytically relevant mutants were used to probe the effect of loop flexibility on catalytic efficiency. The structure of MtFBA in its holoenzyme form is described by S. Pegan et al., Biochemistry. 2013 Feb. 5; 52(5):912-25.

FIG. 1 shows MtFBA's essential role in the gluconeogenesis and glycolysis pathways. Fructose 1,6-bisphosphate (FBP) is depicted in the linear MtFBA substrate form.

Antibiotic Activity of Compounds Derived from 8-Hydroxyquinoline-2-Carboxylic Acid (HCA)

To identify new antibiotics targeting MtFBA, chemical fragments were screened for their ability to simulate the enolate transition state's hydroxamic acid of DHAP with MtFBA's active site Zn(II), but be devoid of groups that would be interfere with pharmaceutical development. 8-hydroxyquinoline-2-carboxylic acid (HCA) and derivatives thereof, as described in more detail below, were identified as having superior activity.

There is no logical basis that would suggest a priori that HCA and related structures would act as selective inhibitors of MtFBA. In fact, the data show that HCA interacts with MtFBA through an induced fit mechanism. In other words, HCA creates its own binding pocket. 8-hydroxyquinoline like derivatives that have been studied previously were viewed as acting on tuberculosis and other bacteria by chelating free metals in solution. Thus, no rational attempt to improve them, or give rise to the 8-hydroxyquinoline like derivatives proposed here to bind selectively with MtFBA would have logically occurred.

FIG. 2 shows X-ray structure of HCA bound to MtFBA. In FIG. 2A HCA (the bicyclic compound) is shown bound to neighboring amino acid residues in MtFBA. The density shell shown around the HCA reflects fo-fc density at 3σ. The density around the amino acid residues reflects 2fo-fc at 1σ for MtFBA residues forming non-hydrophobic interactions with HCA. Dashed lines illustrate specific interactions with water rendered as a cyan sphere. FIG. 2B is another view with MtFBA-PGH structure overlaid. Zn(II) and residues in frame belonging to the MtFBA-PGH structure are rendered in grey. FIG. 2C shows HCA binding cavity on MtFBA. Waters are represented as in panel (A) with two prominent pockets denoted.

Advantages Over Currently Available Antibiotics:

The antibiotic compounds of this invention represents a new class that are structurally divergent from existing antibiotics, for which bacterial resistance has evolved. As Class II FBA is central to *M. tuberculosis* as well as other bacterial and parasitic protozoan organisms, alterations to this enzyme in an effort to build drug-resistance would be deleterious to the bacteria and protozoan. As a result, pathogenic bacteria and protozoan are less likely to be able to build a resistance to 8-hydroxyquinoline-2-carboxylic acid based inhibitors of Class II fructose 1,6-bisphosphate aldolase than previously available antibiotics.

Previously known Class II FBA inhibitors have been substrate mimics. In other words, variations on the Class II FBA substrates dihydroxyacetone or fructose 1,6-bisphosphate. As a result, they have phosphate groups that are required for specificity and potency but also impede their ability to cross the cellular membranes of mammalian cells and tuberculosis. 8-hydroxyquinoline-2-carboxylic acid has no such groups or requirements for them to achieve equal or better inhibition.

HCA analogues according to this invention are drug-like according to Lipinski's rule of 5 and other pharmaceutical guidelines. Using the widely viewed parameters of drug-likeness, MW≤500, clogP≤5, H-bond donors≤5, H-bond acceptors≤10, tPSA≤100, and rotatable bonds≤8, 8-hydroxyquinoline-2-carboxylic acid has a MW of 189.2, clogP of 1.3, two H-bond donors, four H-bond acceptors, and a tPSA of 70.4. Lipinski, C. A, et al., Adv. Drug Delivery Rev. 2001. 46(1-3):3-26; Rees, D. C, et al., Nat Rev Drug Discov, 2004. 3(8):660-72.; Veber, D. F, et al., J Med Chem, 2002. 45(12): 2615-23.

All previous Class II FBA inhibitors have focused on the narrow and highly charged Class II FBAs active sites. This impedes any further addition of chemical groups to enhance in vitro, or in vivo, efficacy. However, HCA and associated analogues alter the MtFBA's active site. By doing so, they generate openings for additional chemical groups that can facilitate further pharmacological improvement.

Human analogues for Class II FBAs do not exist. By all previous Class II FBA inhibitors maintaining similarity to FBA substrates there is an inherent possibility of toxicity via either class I FBAs, or other human enzymes that utilize DHAP, G3P, or FBP. As 8-hydroxyquinoline-2-carboxylic acid and other listed derivatives create a unique binding pocket in Class II FBA and don't mimic FBA substrates, the risk of toxicity by them serving as a substrate for other human enzymes is predictably lower.

Model Compounds

This invention provides antibiotics for tuberculosis and other pathogenic bacteria through the noncompetitive inhibition of *M. tuberculosis* Class II 1,6-bisphosphate aldolase.

FIG. 3 shows similarity of key residues of FBA from different pathogens around about the HCA binding pocket. Due to the conserved nature of Class II 1,6-bisphosphate aldolases, HCA can be used to treat and manage a wide range of other pathogenic bacteria and parasitic eukaryotes.

Model compounds are based on or derivatized from 8-hydroxyquinoline-2-carboxylic acid (HCA). Exemplary are compounds having the structure shown in Formula (I).

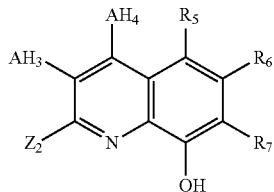

Formula (I)

Exemplary substituents include the following:

$R_7$=H, alkyl, alkenyl, alkynyl, F, Cl, Br, $CF_3$, or OH $R_6$=H, alkyl, alkenyl, alkynyl, F, Cl, Br, or $CF_3$ $R_5$=H, alkyl, alkenyl, alkynyl, F, Cl, Br, $CF_3$, or OH $AH_4$=H, alkyl, alkenyl, alkynyl, aryl, F, Cl, Br, $CF_3$, or OH $AH_3$=H, alkyl, alkenyl, alkynyl, aryl, F, Cl, Br, $CF_3$, or OH $Z_2$=$CO_2H$, $CO_2R$, $CONH_2$, or CONHR, where R is alkyl, alkenyl, alkynyl, aryl, or heteroaryl.

The term "alkyl" as used in this disclosure refers to a branched or unbranched, saturated or unsaturated or cyclic hydrocarbon radical of between 1 and 50 carbon atoms or between 1 and 20 carbon atoms. Unless specified otherwise, an alkyl group may be an unsubstituted hydrocarbyl, or it may be a heteroalkyl in which one or more hydrogen atoms and/or any carbon of the alkyl is replaced by a heteroatom such as N, O, P, or S. Similarly, an alkenyl or alkynyl group may be branched, unbranched, or cyclical; it may be a hydrocarbyl or comprise a heteroatom such as N, O, P, or S.

The term "aryl" refers to an aromatic substituent, which may be a single aromatic ring or multiple aromatic rings that are fused together, linked covalently, or linked to a common group such as a methylene or ethylene biradical. Aryl groups may have between 1 and 50 carbon atoms or between 1 and 20 carbon atoms. Unless specified otherwise, aryl groups may be hydrocarbyl groups, or heteroaryl groups wherein one or more carbon atoms of the aromatic ring(s), substituents or bridges are replaced by a heteroatom(s) such as N, O, P, or S. In some embodiments of the invention, the —OH group depicted in Formula I may be substituted with a sulfhydryl or alkoxyl group. In general terms, $Z_2$ may be a carboxylic acid, ester, alkoxyl group, alcoxylamine, a sulfhydryl derivative, or an aryl or heteroaryl group.

Particular illustrations are as follows:

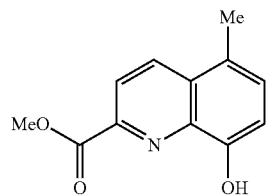

1

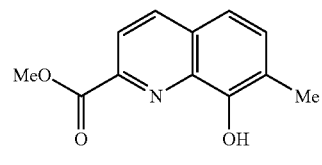

2

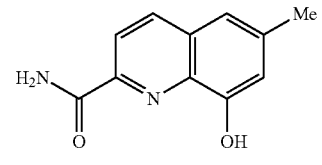

3

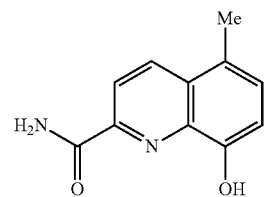

4

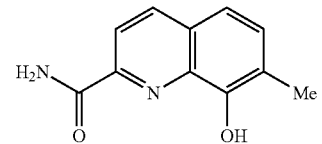

5

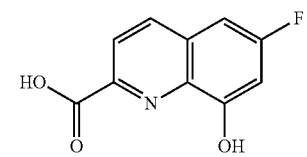

6

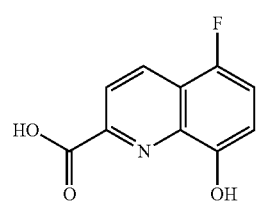

7

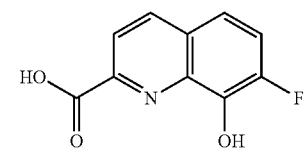

8

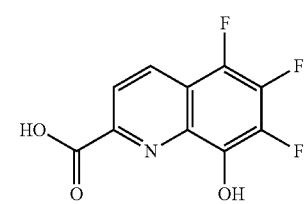

9

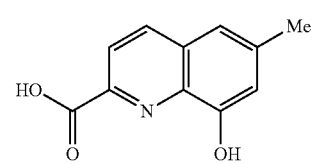

10

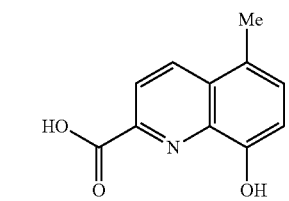

11

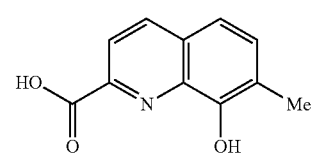

12

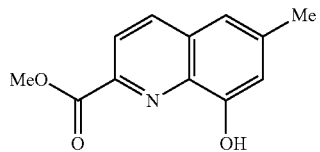

13

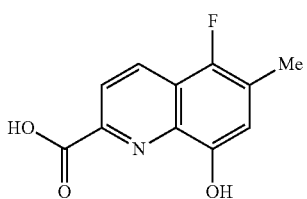

14

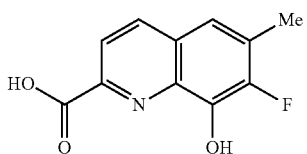

15

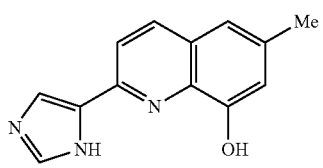

16

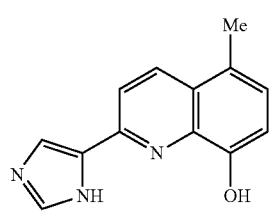

17

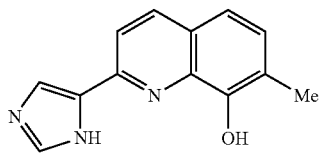

18

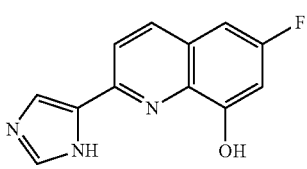 [SMILES: Oc1cc(F)cc2ccc(-c3cnc[nH]3)nc12]

19

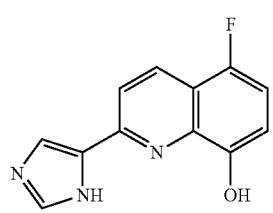

20

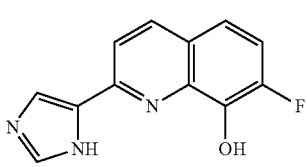

21

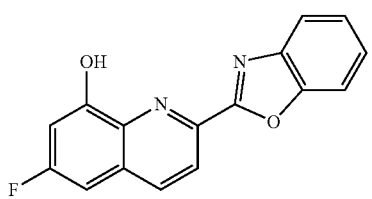

22

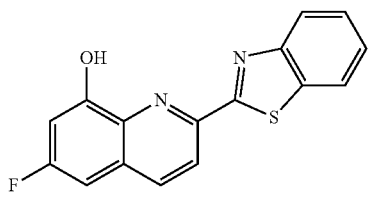 [SMILES: Oc1cc(F)cc2ccc(-c3nc4ccccc4o3)nc12]

23

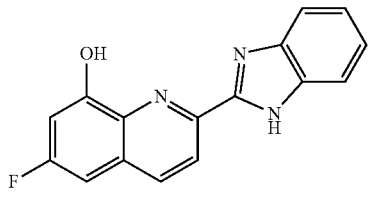 [SMILES: Oc1cc(F)cc2ccc(-c3nc4ccccc4[nH]3)nc12]

24 wherein:
1 8-hydroxy-6-methylquinoline-2-carboxylic acid
2 8-hydroxy-5-methylquinoline-2-carboxylic acid
3 8-hydroxy-7-methylquinoline-2-carboxylic acid
4 methyl 8-hydroxy-6-methylquinoline-2-carboxylate
5 methyl 8-hydroxy-5-methylquinoline-2-carboxylate
6 methyl 8-hydroxy-7-methylquinoline-2-carboxylate
7 8-hydroxy-6-methylquinoline-2-carboxamide
8 8-hydroxy-5-methylquinoline-2-carboxamide
9 8-hydroxy-7-methylquinoline-2-carboxamide
10 6-fluoro-8-hydroxyquinoline-2-carboxylic acid
11 5-fluoro-8-hydroxyquinoline-2-carboxylic acid
12 7-fluoro-8-hydroxyquinoline-2-carboxylic acid
13 5,6,7-trifluoro-8-hydroxyquinoline-2-carboxylic acid
14 5-fluoro-8-hydroxy-6-methylquinoline-2-carboxylic acid
15 7-fluoro-8-hydroxy-6-methylquinoline-2-carboxylic acid
16 2-(1H-imidazol-5-yl)-6-methylquinolin-8-ol
17 2-(1H-imidazol-5-yl)-5-methylquinolin-8-ol
18 2-(1H-imidazol-5-yl)-7-methylquinolin-8-ol
19 6-fluoro-2-(1H-imidazol-5-yl)quinolin-8-ol
20 5-fluoro-2-(1H-imidazol-5-yl)quinolin-8-ol
21 7-fluoro-2-(1H-imidazol-5-yl)quinolin-8-ol
22: 2-(benzo[d]oxazol-2-yl)-6-fluoroquinolin-8-ol
23: 2-(benzo[d]thiazol-2-yl)-6-fluoroquinolin-8-ol
24: 2-(1H-benzo[d]imidazol-2-yl)-6-fluoroquinolin-8-ol In reference to FIG. 8A, some embodiments of the invention optionally contain a pharmacophore that comprises a two ring conjugated system that provide stability for a hydrogen donor at position $R_8$ (depicted in Formula (I) as a hydroxyl group), as well as a chemical moiety containing a hydrogen donor/accepter at position $Z_2$, such as a carboxylic acid. The addition of foliage in the terms of a hydrophobic entity at position $R_6$ and other hydrogen donor/acceptors at $R_7$, $R_5$, $AH_4$, and/or $AH_3$ to facilitate ligand-protein H-bonds may be used to increase potency. Alteration of the zinc interacting pharmacophore could occur by alternating the nitrogen with another nucleophile such as sulfur or oxygen. Also, the carboxylic acid could be substituted with other nucleophile containing groups such as an imidazole ring system.

Preparation

The synthesis of HCA derivatives according to this invention can be achieved by applying the Skraup reaction to commercially available anilines. The reader is generally referred to Manske, R. H, The chemistry of quinolines. Chemical Reviews, 1942. 30(1):113-144.

Referring to FIG. 4A, an analine according to Formula (2) is converted to a bicyclic compound as described in Manske, supra. This process is tolerant of unprotected phenols and results in the formation of differentially substituted quinoline ring systems of Formula (3) in high yields. The quinolines can then be subjected to an established four-step sequence to append the 2-carboxylic acid moiety giving a set of HCA derivatives according to Formula (4). Shrader, W. D. et al., Tetrahedron Letters, 1988. 29(12):1351-1354. These compounds are then tested in binding assays to provide initial SAR data.

Replacement of the 2-carboxylic acid moiety, designated "$Z_2$" in Formula (1), can serve as an additional point of diversity and optimization. Various ester and amide analogs could be prepared using standard organic synthesis. A pyridine ring at the 2-position can also be incorporated into the 8-hydroxyquinoline scaffolds by employing the Friedländer condensation of readily available materials. El Ojaimi et al., Inorganic Chemistry, 2011. 50(21):10966-10973.

The Doebner-Miller reaction (Irving, H. et al., J. Chem. Soc. 1954, 3782-3785) can also be applied for synthesis of HCA derivatives, as depicted in FIG. 4B. This process allows for methyl group incorporation at C2 directly from the cyclization event to give products of Formula (5). A benzylic oxidation to the carboxylic acid is then readily achieved using selenium dioxide ($SeO_2$). Nycz, J. E. et al., J. Mol. Struct. 2013, 1032, 159-168. This method complements the Skraup reaction protocol in preparation of HCA analogs with various R groups on the aniline of Formula (2).

Depending on initial SAR data obtained from binding assays, replacement of the 2-carboxylic acid moiety can then serve as an additional point of diversity. Various ester and amide analogs can be prepared using standard organic synthesis. A pyridine ring at the 2-position can also be incorporated into the 8-hydroxyquinoline scaffolds by employing the Friedländer condensation of readily available materials. Ojaimi, M. E. et al., Inorg. Chem. 2011, 50, 10966-10973.

Testing

Enzymatic activity of candidate antibiotic and antiparasitic compounds of this invention can be assessed using isolated or recombinant Class II FBA of bacterial or parasite origin, preferably derived from or related to the intended target microorganism. Enzymatic activity is measured by contacting the enzyme with a suitable substrate, such as fructose 1,6-bisphosphate, and measuring formation of a product such as dihydroxyacetone phosphate (DHAP) or glyceraldehyde 3-phosphate (GAP). If the activity is measurably lower in the presence of the candidate compound than in its absence, then the compound has FBA inhibitory activity and is a candidate antibiotic and antiparasitic compound. The compound may also be screened with recombinant or isolated Class I FBA (for example, of human or mammalian origin) to determine cross-inhibition. Compounds that specifically inhibit Class II FBA but not Class I FBA are generally preferred.

Alternatively or in addition, compounds can be screened for antibiotic and/or antiparasitic activity by contacting them with the target microorganism, for example, in tissue culture. Efficacy and safety can be confirmed in preclinical animal models and human clinical trials.

Use in Therapy

The essential role of Class II FBAs in bacteria can be illustrated through knockout studies of gram positive and negative bacteria including *M. tuberculosis*, *E. coli*, *Streptomyces galbus*, *Bacillus subtilis*, *Pseudomonas aeruginosa*, *Streptococcus pneumoniae*, and *Candida albicans*. Even when bacteria such as *E. coli* and other autotrophic prokaryotes possess both class I and Class II FBAs, class I FBAs are only conditionally expressed with Class II FBAs being essential.

FIG. 3 shows the high similarity amongst Class II FBAs from different bacteria around HCA induced pocket. Structural alignments of MtFBA a Class IIa FBA with *E. coli*'s Class IIa FBA and that of *B. anthracis*'s Class IIb FBA further reinforces the conserved nature of the HCA induced pocket. Accordingly, the antibiotic compounds of this invention can be employed for treatment of a wide range of bacteria.

With respect to parasites, Class II FBAs in *G. lamblia* (Giardia), *cryptosporidium parvum* (Crypto), *Trypanosoma brucei* (Trypanosomiasis), and *Plasmodium falciparum* (malaria) are predicted to be essential. As with bacteria, Class II FBAs from these protozoan also have high similarity within the hydroxyquinoline-2-carboxylic acid induced Class II FBA pocket. As a result, 8-hydroxyquinoline-2-carboxylic acid based inhibitors could practically be employed to treat or protect against infection by any of these agents, and (by analogy) a broad range of similar parasitic organisms.

One or more HCA compounds and derivatives according to this invention may be formulated in a suitable excipient or carrier for administration orally, by injection, or topically. For oral administration, a dose of 1 to 25 mg/kg/day (or 5 to 10 mg/kg/day) may constitute a therapeutically effective amount. When the compound is used as part of a soap or disinfectant, a concentration of 0.05 to 1%, or about 0.3% (wt/wt) may be suitable. A "therapeutically effective amount" of a drug refers to an amount of a drug that, when administered to a patient to treat a condition such as cancer, will have a beneficial effect, such as alleviation, amelioration, palliation or elimination infection, a reduction in symptoms or signs of the disease, or cosmetic improvement.

Suitable dosage forms formulated as a medicament can be produced and distributed as a the combination or kit which may also contain or be marketed in combination with written instructions that direct the clinician on the use of the elements of the kit for chemotherapy in accordance with the invention.

EXAMPLES

Figure 5:
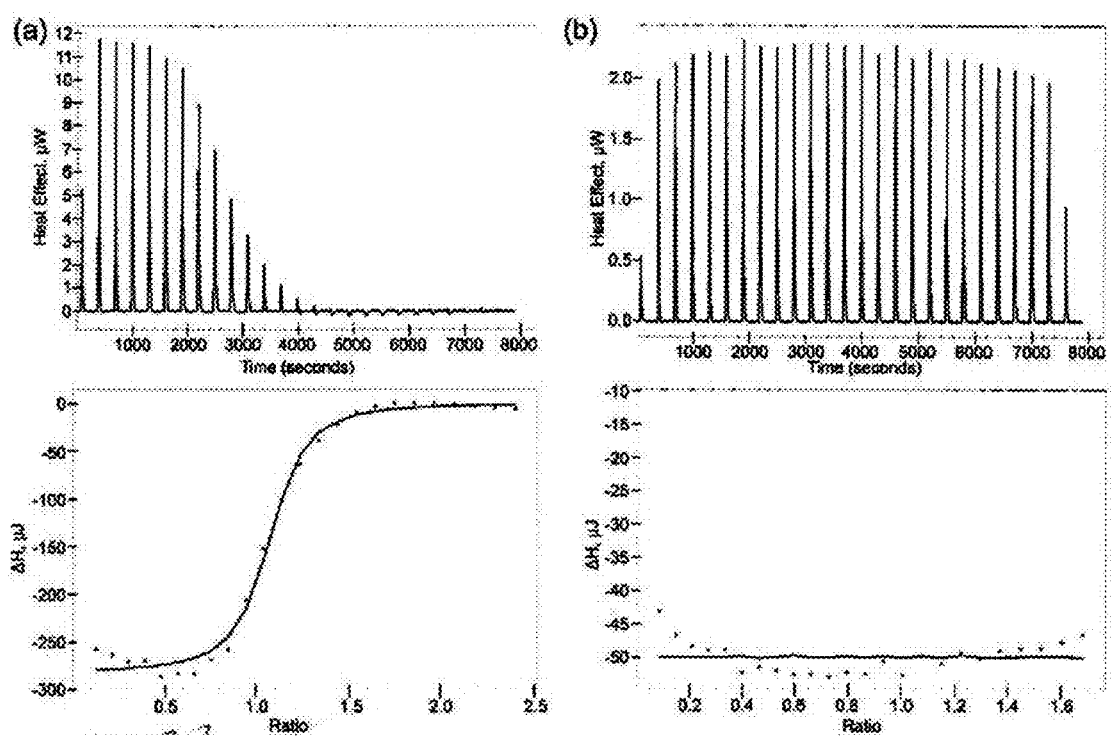

FIG. 5 provides data from the calorimetric titration of 8-hydroxyquinoline-2-carboxylic acid (HCA). Left-side panels show 5 mM Regis 5 titrated into 700 μM of MtFBA demonstrating a Kd=6.94±0.97 μM, ΔH=−28.73±0.58 kJ $mol^{-1}$, ΔS=2.44±3.12 J $mol^{-1}$ $K^{-1}$, and n=0.94±0.14. Right-side panels show 1 mM Regis 5 titrated into MtFBA buffer with 200 μM $ZnCl_2$, exhibiting no appreciable binding. Top graphs represent raw heat data and bottom graphs are integrated heat peaks gained at 25° C. from 25 injections of Regis 5 into 170 μL of 20 mM Tricine pH 8.0, 100 mM NaCl, and either (a) 700 μM MtFBA with 100 μM $ZnCl_2$ or (b) 200 μM $ZnCl_2$. Data sets were collected in duplicate, analyzed with NanoAnalyze™ software, and fit to an independent model concurrently with a bank constant model to adjust for a heat of dilution. The line shows the best fit to an independent model.

FIG. 6 provide MtFBA inhibitor properties of HCA. FIG. 6A is a Lineweaver-Burk plot of the kinetics of inhibition of MtFBA by 8-hydroxyquinoline-2-carboxylic acid against MtFBA for varying concentrations of FBP (●) 9.375 μM, (○) 18.75 µM, (▼) 37.5 µM, and (■) 150 µM. The inset is a Michaelis-Menten plot of inhibition of MtFBA by serial dilutions of 8-hydroxyquinoline-2-carboxylic acid against MtFBA demonstrating an $IC_{50}=17\pm2.1$ µM. FIG. 6B is Isothermal Titration calorimetry (ITC) of HCA binding to MtFBA (solid curved line), or blank Zn(II) buffer (top dotted line).

FIG. 7A is the amino acid sequence alignment of Class II FBAs from pathogenic bacteria. FBAs are from the H37RV strain of *M. tuberculosis* (protein accession code NP_334786) (SEQ. ID NO:1), *Yersinia pestis* (protein accession code ZP_04518851) (SEQ. ID NO:2), *Staphylococcus aureus* (protein accession code QHE75) (SEQ. ID NO:3), *Bacillus anthracia* (PDB code 3Q94) (SEQ. ID NO:4), and *Klebsiella pneumonia* (protein accession code ZP_14594173) (SEQ. ID NO:5). Asterisks denote residues involved in hydrophobic interactions as well as hydrogen bonds formed between MtFBA and HCA. FIG. 7B is the amino acid sequence of human Class I FBA (SEQ. ID NO:6).

FIG. 8 is another depiction of the binding of 8-hydroxyquinoline-2-carboxylic acid (HCA) to tuberculosis MtFBA. FIG. 8A shows the general chemical structure of 8-hydroxyquinoline-2-carboxylic acid and its chemical scaffold. FIG. 8B is the X-ray crystal structure of 8-hydroxyquinoline-2-carboxylic acid bound to MtFBA. FIG. 8C is a surface rendering to reveal 8-hydroxyquinoline-2-carboxylic acid bound to MtFBA binding cavity.

The following table shows the limited structure activity relationship of a portion of the chemical space surrounding the active site zinc interacting pharmacophore of 8-hydroxyquinoline-2-carboxylic acid. Numbering of the substituents is in accordance with FIG. 8A.

Figure 10:
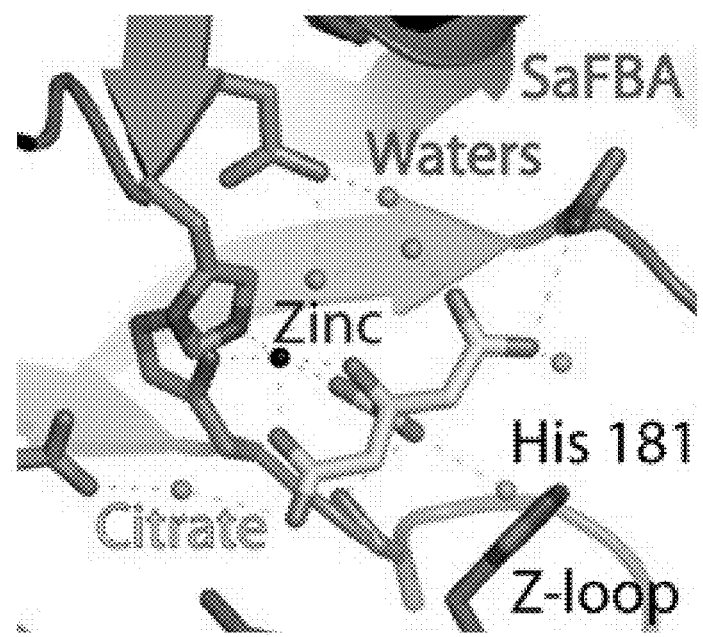
FIG. 10 shows the active site for *S. aureus* FBA (SaFBA) in the crystal structure with citrate bound in the HCA-like pocket. Z-loop flexibility is characteristic of both MtFBA and SaFBA, a likely common mode of inhibition by HCA.

FIG. 10 shows the active site for SaFBA in the crystal structure with citrate bound in the HCA-like pocket. The X-ray structure was determined to 2.1 Å resolution of the class IIb FBA from MRSA (SaFBA). A citrate molecule was visualized within the SaFBA's active sites occupying a pocket similarly to that formed by HCA in the class II FBA originating from *Mycobacterium tuberculosis* (MtFBA). The binding of citrate by SaFBA, as was the case with HCA and MtFBA, displaced the structural motif, known as the Z-loop, in SaFBA. As a result, the SaFBA-citrate complex demonstrates that Z-loop flexibility is not limited to just MtFBA. With HCA also inhibiting SaFBA with comparable potency, the SaFBA-citrate complex points to a likely common mode of inhibition of HCA for SaFBA.

Figure 11:
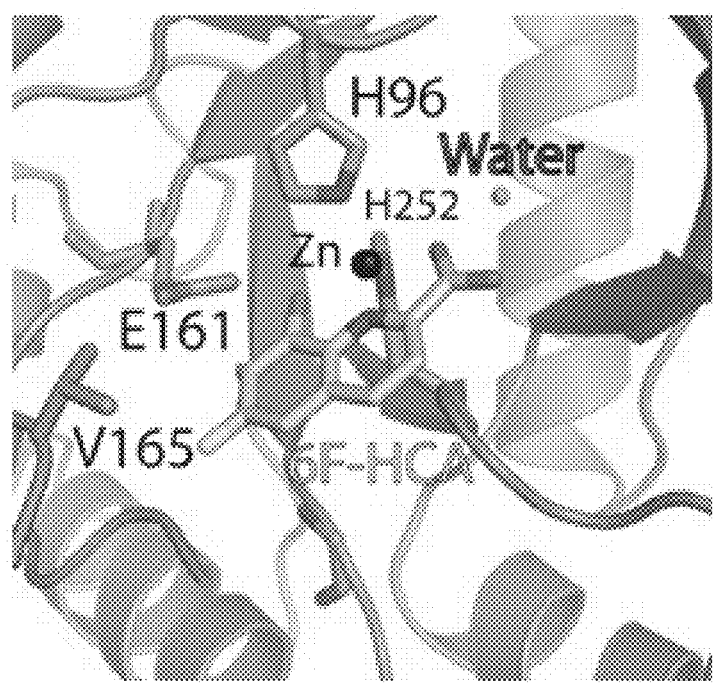
FIG. 11 shows the binding of 6F substituted HCA bound to MtFBA. This increases potency towards the enzyme by 50%, and further validates that the HCA scaffold is acting through displacement of the Z-loop.

FIG. 11 shows the 6F derivative of HCA bound to MtFBA. Using the X-ray structure of class II FBA originating from *Mycobacterium tuberculosis* (MtFBA) bound to HCA, the HCA scaffold's potency toward the enzyme was improved by the addition of fluorine at position 6 (6F-HCA). Adding fluorine at position 6 was sourced from the fact that a void in the MtFBA-HCA structure was present by valine residue 165. A 2.1 Å X-ray structure of 6F-HCA bound to MtFBA found not only to occupy this space, but also increase potency toward the enzyme by 50%. This further validates that the HCA scaffold is acting through displace the Z-loop. Activity of compounds based on the HCA scaffold can be rationally improved by addition of functional groups, as illustrated earlier in this disclosure.

Additional Information

1. *Global tuberculosis control—surveillance, planning, financing*, 2008, World Health Organization: Geneva, Switzerland. p. 1-5.

| Compound | R8 | R7 | R6 | R5 | AH4 | AH3 | Z2 | % Inhibition at 1 mM | $IC_{50}$ (µM) |
|---|---|---|---|---|---|---|---|---|---|
| 5 | OH | H | H | H | H | H | COOH | 95 ± 4.1 | 14 ± 2.0 |
| 6 | OH | H | H | H | H | H | H | 54 ± 18 | 300 ± 67 |
| 7 | OH | H | H | H | H | H | $NH_2$ | 56 ± 2.6 | NA |
| 8 | OH | H | H | H | H | H | OH | 65 ± 4.1 | NA |
| 18 | $NH_2$ | H | H | H | H | H | H | 68 ± 2.2 | 79 ± 10 |
| 19 | H | H | H | H | H | H | COOH | 11 ± 0.05 | NA |
| 23 | $NH(SO_2)CH_3$ | H | H | H | H | H | H | 32 ± 1.1 | NA |
| 28 | H | H | H | H | H | H | OH | 12 ± 9.5 | NA |
| 31 | COOH | H | H | H | H | H | H | 9.9 ± 1.6 | NA |
| 32 | H | H | H | H | H | H | $NH_2$ | 12 ± 9.5 | NA |
| 34 | OH | H | H | H | H | H | $NH(SO_2)CH_3$ | 12 ± 5.4 | 570 ± 87 |
| 35 | $NO_2$ | H | H | H | H | H | COOH | 31 ± 8.0 | NA |
| 36 | $NH_2$ | H | H | H | H | H | COOH | 22 ± 6.2 | NA |
| 43 | OH | H | H | H | OH | H | COOH | 12 ± 4.4 | NA |

Figure 9:
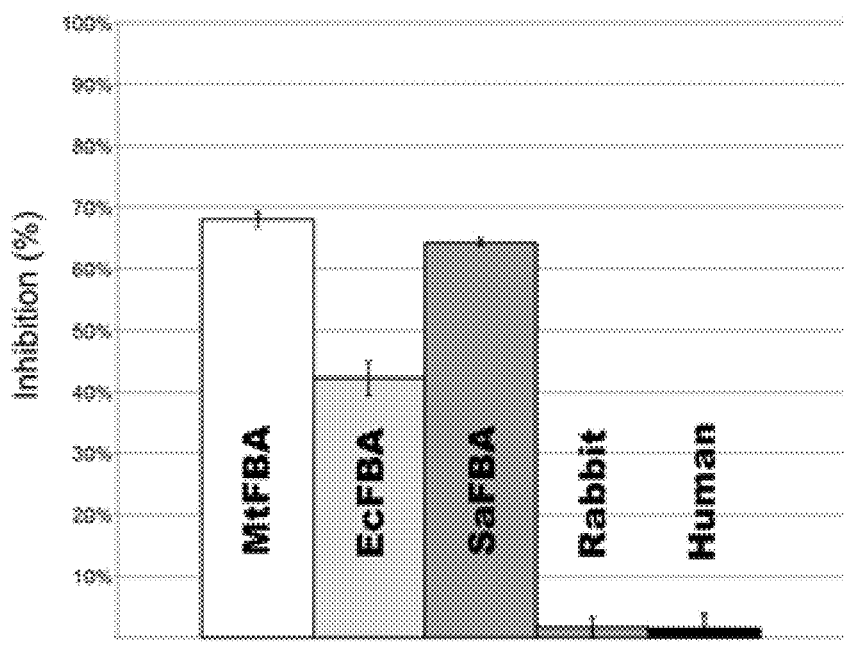
FIG. 9 illustrates HCA's potential as a class II FBA broad-spectrum inhibitor. A single concentration of HCA at 25 µM inhibits class IIa FBA isolated from *E. coli* and class IIb FBA originating from methicillin-resistant *S. aureus* (MRSA).

FIG. 9 illustrates HCA's potential as a class II FBA broad-spectrum inhibitor. Class II FBAs can be broken down into two families (a/b) whose distribution among bacterium is independent of Gram staining determined phylogenetic groups. In this illustration, a single concentration of HCA at 25 µM was tested for the inhibition of class IIa FBA isolated from *E. coli* and class IIb FBA originating from methicillin-resistant *S. aureus* (MRSA).

As shown in FIG. 9, HCA demonstrated a 42.2±2.8% inhibition against *E. coli* and 64.3±0.6% inhibition against MRSA. Error bars represent standard deviations from the average. To demonstrate that HCA is selective for class II FBAs over their class I counterparts, class I FBAs isolated from both rabbit and human muscle were tested against HCA. Unlike class II FBAs, HCA showed no inhibitory affects against either class I FBA even at concentrations as high as 1 mM, which forecasts a low probability of toxicity through class I FBA inhibition in humans.

2. World Health Organization, *Global tuberculosis report 2012 (in IRIS)*. 2012, Geneva: World Health Organization. viii, 272 p.
3. World Health Organization, UNAIDS, and UNICEF, *Global HIV/AIDS response: epidemic update and health sector progress towards universal access: progress report 2011*. 2011, Geneva: World Health Organization. viii, 224 p.
4. *Implementing the Stop TB Strategy: a handbook for national tuberculosis*, 2008, World Health Organization: Geneva, Switzerland. p. 1-198.
5. Perez, F. and D. Van Duin, *Carbapenem-resistant Enterobacteriaceae: A menace to our most vulnerable patients*. Cleve Clin J Med, 2013. 80(4):225-33.
6. Scheffler, R. J, et al., *Antimicrobials, drug discovery, and genome mining*. Appl Microbiol Biotechnol, 2013. 97(3): 969-78.

7. Froude, J. W, et al., *Antibodies for biodefense*. MAbs, 2011. 3(6):517-27.
8. de la Paz Santangelo, M, et al., *Glycolytic and non-glycolytic functions of Mycobacterium tuberculosis fructose-1,6-bisphosphate aldolase, an essential enzyme produced by replicating and non-replicating bacilli*. J Biol Chem, 2011. 286(46):40219-31.
9. Fonvielle, M, et al., *Synthesis and biochemical evaluation of selective inhibitors of Class II fructose bisphosphate aldolases: towards new synthetic antibiotics*. Chemistry, 2008. 14(28):8521-9.
10. Fonvielle, M, et al., *New highly selective inhibitors of Class II fructose-1,6-bisphosphate aldolases*. Bioorg Med Chem Lett, 2004. 14(11):2923-6.
11. Gallein, A, et al., *Structural insights into the substrate binding and stereoselectivity of giardia fructose-1,6-bisphosphate aldolase*. Biochemistry, 2009. 48(14):3186-96.
12. Gerdes, S. Y, et al., *Experimental determination and system level analysis of essential genes in Escherichia coli MG1655*. J Bacteriol, 2003. 185(19):5673-84.
13. Labbe, G, et al., *Evaluation of four microbial Class II fructose 1,6-bisphosphate aldolase enzymes for use as biocatalysts*. Protein Expr Purif, 2011. 80(2):224-33.
14. Labbe, G, et al., *Development of metal-chelating inhibitors for the Class II fructose 1,6-bisphosphate (FBP) aldolase*. J Inorg Biochem, 2012. 112:49-58.
15. Pegan, S. D, et al., *Active site loop dynamics of a Class IIa fructose 1,6-bisphosphate aldolase from Mycobacterium tuberculosis*. Biochemistry, 2013. 52(5):912-25.
16. Pegan, S. D, et al., *Structural basis for catalysis of a tetrameric Class IIa fructose 1,6-bisphosphate aldolase from Mycobacterium tuberculosis*. J Mol Biol, 2009. 386(4):1038-53.
17. Ramsaywak, P. C, et al., *Molecular cloning, expression, purification, and characterization of fructose 1,6-bisphosphate aldolase from Mycobacterium tuberculosis—a novel Class IIA tetramer*. Protein Expr Purif, 2004. 37(1): 220-8.
18. Gavalda, S, et al., *N-Sulfonyl hydroxamate derivatives as inhibitors of Class II fructose-1,6-diphosphate aldolase*. Bioorg Med Chem Lett, 2005. 15(24):5375-7.
19. Li, Z, et al., *Rational design, synthesis and evaluation of first generation inhibitors of the Giardia lamblia fructose-1,6-biphosphate aldolase*. J Inorg Biochem, 2011. 105(4): 509-17.
20. Manske, R. H, *The chemistry of quinolines*. Chemical Reviews, 1942. 30(1):113-144.
21. Shrader, W. D, et al., *Synthesis of a Novel Hexadentate Chelating Agent Based on 8-Hydroxyquinoline*. Tetrahedron Letters, 1988. 29(12):1351-1354.
22. El Ojaimi, M. and R. P. Thummel, *Polydentate Analogues of 8-Hydroxyquinoline and Their Complexes with Ruthenium*. Inorganic Chemistry, 2011. 50(21):10966-10973.
23. Baba, T, et al., *Construction of Escherichia coli K-12 in-frame, single-gene knockout mutants: the Keio collection*. Mol Syst Biol, 2006. 2:2006 0008.
24. Giaever, G, et al., *Functional profiling of the Saccharomyces cerevisiae genome*. Nature, 2002. 418(6896):387-91.
25. Jacobs, M. A, et al., *Comprehensive transposon mutant library of Pseudomonas aeruginosa*. Proc Natl Acad Sci USA, 2003. 100(24):14339-44.
26. Kobayashi, K, et al., *Essential Bacillus subtilis genes*. Proc Natl Acad Sci USA, 2003. 100(8):4678-83.
27. Liberati, N. T, et al., *An ordered, nonredundant library of Pseudomonas aeruginosa strain PA14 transposon insertion mutants*. Proc Natl Acad Sci USA, 2006. 103(8):2833-8.
28. Rodaki, A, T. Young, and A. J. Brown, *Effects of depleting the essential central metabolic enzyme fructose-1,6-bisphosphate aldolase on the growth and viability of Candida albicans: implications for antifungal drug target discovery*. Eukaryot Cell, 2006. 5(8):1371-7.
29. Sassetti, C. M, D. H. Boyd, and E. J. Rubin, *Genes required for mycobacterial growth defined by high density mutagenesis*. Mol Microbiol, 2003. 48(1):77-84.
30. Song, J. H, et al., *Identification of essential genes in Streptococcus pneumoniae by allelic replacement mutagenesis*. Mol Cells, 2005. 19(3):365-74.
31. Wehmeier, U. F, *Molecular cloning, nucleotide sequence and structural analysis of the Streptomyces galbus DSM40480 fda gene: the S. galbus fructose-1,6-bisphosphate aldolase is a member of the Class II aldolases*. FEMS Microbiol Lett, 2001. 197(1):53-8.
32. Stribling, D. and R. N. Perham, *Purification and characterization of two fructose diphosphate aldolases from Escherichia coli (Crookes' strain)*. Biochem J, 1973. 131 (4):833-41.
33. Scamuffa, M. D. and R. M. Caprioli, *Comparison of the mechanisms of two distinct aldolases from Escherichia coli grown on gluconeogenic substrates*. Biochim Biophys Acta, 1980. 614(2):583-90.
34. Henze, K, et al., *Sequence and phylogenetic position of a Class H aldolase gene in the amitochondriate protist, Giardia lamblia*. Gene, 1998. 222(2):163-8.
35. Clayton, C. E, *Structure and regulated expression of genes encoding fructose biphosphate aldolase in Trypanosoma brucei*. EMBO J, 1985. 4(11):2997-3003.
36. Knapp, B, E. Hundt, and H. A. Kupper, *Plasmodium falciparum aldolase: gene structure and localization*. Mol Biochem Parasitol, 1990. 40(1):1-12.
37. Lipinski, C. A, et al., *Experimental and computational approaches to estimate solubility and permeability in drug discovery and development settings*. Advanced Drug Delivery Reviews, 2001. 46(1-3):3-26.
38. Rees, D. C, et al., *Fragment-based lead discovery*. Nat Rev Drug Discov, 2004. 3(8):660-72.
39. Veber, D. F, et al., *Molecular properties that influence the oral bioavailability of drug candidates*. J Med Chem, 2002. 45(12):2615-23.

For all purposes in the United States of America, each and every publication and patent document cited herein is incorporated herein by reference as if each such publication or document was specifically and individually indicated to be incorporated herein by reference.

While the invention has been described with reference to the specific embodiments, changes can be made and equivalents can be substituted to adapt to a particular context or intended use, thereby achieving benefits of the invention without departing from the scope of what is claimed.

The invention claimed is:

1. A compound according to Formula (I)

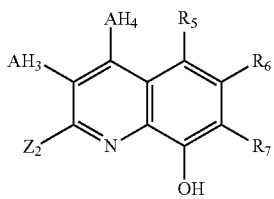

Formula (I)

wherein $R_7$=H, alkyl, alkenyl, alkynyl, F, Cl, Br, $CF_3$, or OH $R_6$=F $R_5$=H, alkyl, alkenyl, alkynyl, F, Cl, Br, $CF_3$, or OH $AH_4$=H, alkyl, alkenyl, alkynyl, aryl, F, Cl, Br, $CF_3$, or OH $AH_3$=H, alkyl, alkenyl, alkynyl, aryl, F, Cl, Br, $CF_3$, or OH $Z_2$=$CO_2H$, $CO_2R$, $CONH_2$, CONHR, aryl, or heteroaryl, wherein the compound is one of the following compounds:

6-fluoro-8-hydroxyquinoline-2-carboxylic acid, 5,6,7-trifluoro-8-hydroxyquinoline-2-carboxylic acid, 6-fluoro-2-(1H-imidazol-5-yl)quinolin-8-ol, 2-(benzo[d]oxazol-2-yl)-6-fluoroquinolin-8-ol, 2-(benzo[d]thiazol-2-yl)-6-fluoroquinolin-8-ol, and 2-(1H-benzo[d]limidazol-2-yl)-6-fluoroquinolin-8-ol.

2. The compound of claim 1, which inhibits Class II fructose 1,6-bisphosphate aldolase (FBA) of *M. tuberculosis* (SEQ. ID NO:1), but not Class I FBA of *homo sapiens* (SEQ. ID NO:6).

3. A pharmaceutical product comprising a compound according to claim 1 in a pharmaceutical excipient formulated for oral administration.

4. A compound according to claim 1, formulated as a soap or disinfectant.

5. The compound 6-fluoro-8-hydroxyquinoline-2-carboxylic acid

6. A compound according to claim 1, which is 5,6,7-trifluoro-8-hydroxyquinoline-2-carboxylic acid

7. The compound 6-fluoro-2-(1H-imidazol-5-yl)quinolin-8-ol

8. A compound according to claim 1, which is 2-(benzo[d]oxazol-2-yl)- 6-fluoroquinolin-8-ol

9. A compound according to claim 1, which is 2-(benzo[d]thiazol-2-yl)- 6-fluoroquinolin-8-ol

10. A compound according to claim 1, which is 2-(1H-benzo[d]imidazol-2-yl)- 6-fluoroquinolin-8-ol

11. A pharmaceutical product comprising a composition according to claim 3 packaged with instructions for treatment or prevention of a bacterial or parasitic infection.

* * * * *

SEQUENCE LISTING

<160> NUMBER OF SEQ ID NOS: 6

<210> SEQ ID NO 1
<211> LENGTH: 338
<212> TYPE: PRT
<213> ORGANISM: Mycobacterium tuberculosis

<400> SEQUENCE: 1

Met Pro Ile Ala Thr Pro Glu Val Tyr Ala Glu Met Leu Gly Gln Ala
1               5                   10                  15

Lys Gln Asn Ser Tyr Ala Phe Pro Ala Ile Asn Cys Thr Ser Ser Glu
            20                  25                  30

Thr Val Asn Ala Ala Ile Lys Gly Phe Ala Asp Ala Gly Ser Asp Gly
                35                  40                  45

Ile Ile Gln Phe Ser Thr Gly Gly Ala Glu Phe Gly Ser Gly Leu Gly
        50                  55                  60

Val Lys Asp Met Val Thr Gly Ala Val Ala Leu Ala Glu Phe Thr His
65                  70                  75                  80

Val Ile Ala Ala Lys Tyr Pro Val Asn Val Ala Leu His Thr Asp His
                85                  90                  95

Cys Pro Lys Asp Lys Leu Asp Ser Tyr Val Arg Pro Leu Leu Ala Ile
            100                 105                 110

Ser Ala Gln Arg Val Ser Lys Gly Gly Asn Pro Leu Phe Gln Ser His
                115                 120                 125

Met Trp Asp Gly Ser Ala Val Pro Ile Asp Glu Asn Leu Ala Ile Ala
130                 135                 140

Gln Glu Leu Leu Lys Ala Ala Ala Ala Lys Ile Ile Leu Glu Ile Glu
145                 150                 155                 160

Glu Ile Gly Val Val Gly Gly Glu Glu Asp Gly Val Ala Asn Glu Ile
                165                 170                 175

Asn Glu Lys Leu Tyr Thr Ser Pro Glu Asp Phe Glu Lys Thr Ile Glu
            180                 185                 190

Ala Leu Gly Ala Gly Glu His Gly Lys Tyr Leu Leu Ala Ala Thr Phe
                195                 200                 205

Gly Asn Val His Gly Val Tyr Lys Pro Gly Asn Val Lys Leu Arg Pro
210                 215                 220

Asp Ile Leu Ala Gln Gly Gln Gln Val Ala Ala Lys Leu Gly Leu
225                 230                 235                 240

Pro Ala Asp Ala Lys Pro Phe Asp Phe Val Phe His Gly Gly Ser Gly
                245                 250                 255

Ser Leu Lys Ser Glu Ile Glu Glu Ala Leu Arg Tyr Gly Val Val Lys
            260                 265                 270

Met Asn Val Asp Thr Asp Thr Gln Tyr Ala Phe Thr Arg Pro Ile Ala
                275                 280                 285

Gly His Met Phe Thr Asn Tyr Asp Gly Val Leu Lys Val Asp Gly Glu
290                 295                 300

Val Gly Val Lys Lys Val Tyr Asp Pro Arg Ser Tyr Leu Lys Lys Ala
305                 310                 315                 320

Glu Ala Ser Met Ser Gln Arg Val Val Gln Ala Cys Asn Asp Leu His
                325                 330                 335

Cys Ala

<210> SEQ ID NO 2
<211> LENGTH: 356
<212> TYPE: PRT
<213> ORGANISM: Yersinia pestis

<400> SEQUENCE: 2

Met Ser Lys Ile Phe Asp Phe Val Lys Pro Gly Val Ile Thr Gly Asp
1               5                   10                  15

-continued

Asp Val Gln Lys Val Phe Ala Val Ala Lys Glu Asn Asn Phe Ala Leu
            20                  25                  30

Pro Ala Val Asn Cys Val Gly Thr Asp Ser Ile Asn Ala Val Leu Glu
        35                  40                  45

Thr Ala Ala Lys Val Arg Ala Pro Val Ile Val Gln Phe Ser Asn Gly
    50                  55                  60

Gly Ala Ala Phe Ile Ala Gly Lys Gly Val Lys Thr Asp Ala Pro Gln
65                  70                  75                  80

Gly Ala Ala Ile Leu Gly Ala Ile Ser Gly Ala His His Val His Gln
                85                  90                  95

Met Ala Glu His Tyr Gly Val Pro Val Ile Leu His Thr Asp His Cys
            100                 105                 110

Ala Lys Lys Leu Leu Pro Trp Leu Asp Gly Leu Leu Asp Ala Gly Glu
        115                 120                 125

Lys His Phe Ala Ala Thr Gly Lys Pro Leu Phe Ser Ser His Met Ile
    130                 135                 140

Asp Leu Ser Glu Glu Ser Leu Glu Glu Asn Ile Glu Ile Cys Ser Lys
145                 150                 155                 160

Tyr Leu Thr Arg Met Ser Lys Ile Gly Met Thr Leu Glu Ile Glu Leu
                165                 170                 175

Gly Cys Thr Gly Gly Glu Glu Asp Gly Val Asp Asn Ser His Met Asp
            180                 185                 190

Ala Ser Ser Leu Tyr Thr Gln Pro Gln Asp Val Asp Tyr Ala Tyr Glu
        195                 200                 205

Lys Leu Asn Ala Ile Ser Pro Arg Phe Thr Ile Ala Ala Ser Phe Gly
    210                 215                 220

Asn Val His Gly Val Tyr Lys Pro Gly Asn Val Lys Leu Thr Pro Thr
225                 230                 235                 240

Ile Leu Arg Asp Ser Gln Asp Tyr Val Ser Lys His Asn Leu Pro
                245                 250                 255

His Asn Ser Leu Asn Phe Val Phe His Gly Gly Ser Gly Ser Thr Ala
            260                 265                 270

Glu Glu Ile Lys Glu Ala Val Ser Tyr Gly Val Val Lys Met Asn Ile
        275                 280                 285

Asp Thr Asp Thr Gln Trp Ala Thr Trp Glu Gly Ile Leu Asn Tyr Tyr
    290                 295                 300

Lys Lys Asn Glu Gly Tyr Leu Gln Gly Gln Leu Gly Asn Pro Glu Gly
305                 310                 315                 320

Ala Asp Lys Pro Asn Lys Lys Tyr Tyr Asp Pro Arg Val Trp Leu Arg
                325                 330                 335

Ala Ala Gln Val Thr Met Ile Thr Arg Leu Glu Leu Ala Phe Lys Glu
            340                 345                 350

Leu Asn Ala Ile
        355

<210> SEQ ID NO 3
<211> LENGTH: 282
<212> TYPE: PRT
<213> ORGANISM: Staphylococcus aureus

<400> SEQUENCE: 3

Met Pro Leu Val Ser Met Lys Glu Met Leu Ile Asp Ala Lys Glu Asn
1               5                   10                  15

Gly Tyr Ala Val Gly Gln Tyr Asn Ile Asn Asn Leu Glu Phe Thr Gln
            20                  25                  30

```
Ala Ile Leu Glu Ala Ser Gln Glu Glu Asn Ala Pro Val Ile Leu Gly
            35                  40                  45

Val Ser Glu Gly Ala Ala Arg Tyr Met Ser Gly Phe Tyr Thr Ile Val
 50                  55                  60

Lys Met Val Glu Gly Leu Met His Asp Leu Asn Ile Thr Ile Pro Val
 65                  70                  75                  80

Ala Ile His Leu Asp His Gly Ser Ser Phe Glu Lys Cys Lys Glu Ala
            85                  90                  95

Ile Asp Ala Gly Phe Thr Ser Val Met Ile Asp Ala Ser His Ser Pro
            100                 105                 110

Phe Glu Glu Asn Val Ala Thr Thr Lys Lys Val Val Glu Tyr Ala His
            115                 120                 125

Glu Lys Gly Val Ser Val Glu Ala Glu Leu Gly Thr Val Gly Gly Gln
130                 135                 140

Glu Asp Asp Val Val Ala Asp Gly Ile Ile Tyr Ala Asp Pro Lys Glu
145                 150                 155                 160

Cys Gln Glu Leu Val Glu Lys Thr Gly Ile Asp Ala Leu Ala Pro Ala
            165                 170                 175

Leu Gly Ser Val His Gly Pro Tyr Lys Gly Glu Pro Lys Leu Gly Phe
            180                 185                 190

Lys Glu Met Glu Glu Ile Gly Leu Ser Thr Gly Leu Pro Leu Val Leu
            195                 200                 205

His Gly Gly Thr Gly Ile Pro Thr Lys Asp Ile Gln Lys Ala Ile Pro
210                 215                 220

Phe Gly Thr Ala Lys Ile Asn Val Asn Thr Glu Asn Gln Ile Ala Ser
225                 230                 235                 240

Ala Lys Ala Val Arg Asp Val Leu Asn Asp Lys Glu Val Tyr Asp
            245                 250                 255

Pro Arg Lys Tyr Leu Gly Pro Ala Arg Glu Ala Ile Lys Glu Thr Val
            260                 265                 270

Lys Gly Lys Ile Lys Glu Phe Gly Thr Ser
            275                 280

<210> SEQ ID NO 4
<211> LENGTH: 282
<212> TYPE: PRT
<213> ORGANISM: Bacilllus anthracis

<400> SEQUENCE: 4

Met Pro Leu Val Ser Met Lys Glu Met Leu Asn Lys Ala Leu Glu Gly
 1               5                  10                  15

Lys Tyr Ala Val Gly Gln Phe Asn Met Asn Asn Leu Glu Trp Thr Gln
            20                  25                  30

Ala Ile Leu Ala Ala Glu Glu Lys Ser Pro Val Ile Leu Gly
            35                  40                  45

Val Ser Glu Gly Ala Ala Arg His Met Thr Gly Phe Lys Thr Val Val
 50                  55                  60

Ala Met Val Lys Ala Leu Ile Glu Glu Met Asn Ile Thr Val Pro Val
 65                  70                  75                  80

Ala Ile His Leu Asp His Gly Ser Ser Phe Glu Lys Cys Lys Glu Ala
            85                  90                  95

Ile Asp Ala Gly Phe Thr Ser Val Met Ile Asp Ala Ser His His Pro
            100                 105                 110

Phe Glu Glu Asn Val Glu Thr Thr Lys Lys Val Val Glu Tyr Ala His
```

```
            115                 120                 125
Ala Arg Asn Val Ser Val Glu Ala Glu Leu Gly Thr Val Gly Gly Gln
        130                 135                 140

Glu Asp Asp Val Ile Ala Glu Gly Val Ile Tyr Ala Asp Pro Ala Glu
145                 150                 155                 160

Cys Lys His Leu Val Glu Ala Thr Gly Ile Asp Cys Leu Ala Pro Ala
                165                 170                 175

Leu Gly Ser Val His Gly Pro Tyr Lys Gly Glu Pro Asn Leu Gly Phe
            180                 185                 190

Ala Glu Met Glu Gln Val Arg Asp Phe Thr Gly Val Pro Leu Val Leu
        195                 200                 205

His Gly Gly Thr Gly Ile Pro Thr Ala Asp Ile Glu Lys Ala Ile Ser
    210                 215                 220

Leu Gly Thr Ser Lys Ile Asn Val Asn Thr Glu Asn Gln Ile Glu Phe
225                 230                 235                 240

Thr Lys Ala Val Arg Glu Val Leu Asn Lys Asp Gln Glu Val Tyr Asp
                245                 250                 255

Pro Arg Lys Phe Ile Gly Pro Gly Arg Asp Ala Ile Lys Ala Thr Val
            260                 265                 270

Ile Gly Lys Ile Arg Glu Phe Gly Ser Asn
        275                 280

<210> SEQ ID NO 5
<211> LENGTH: 283
<212> TYPE: PRT
<213> ORGANISM: Klebsiella pneumonia

<400> SEQUENCE: 5

Met Leu Val Ser Met Lys Asp Met Leu Gln His Ala Leu Arg Asp Gly
1               5                   10                  15

Tyr Ala Val Gly Gln Phe Asn Ile Asn Asn Leu Glu Trp Val Gly Ala
            20                  25                  30

Val Leu Ser Thr Ala Gln Gln Cys Arg Ser Pro Val Ile Leu Gly Val
        35                  40                  45

Ser Gly Gly Thr Val Lys His Met Leu Gly Leu Lys Cys Ile His Asp
    50                  55                  60

Ile Val Val Asn Ala Met Glu Tyr Leu His Ile Asp Val Pro Val Ala
65                  70                  75                  80

Leu His Leu Asp His Gly Thr Ser Arg Glu Ala Cys Glu Ala Ala Ile
                85                  90                  95

Ala Ala Gly Phe Ser Ser Ile Met Phe Asp Gly Ser His Leu Pro Phe
            100                 105                 110

Arg Glu Asn Leu Ala Ile Thr Arg His Leu Val Thr Leu Ala His Ser
        115                 120                 125

Lys Gly Ile Ser Val Glu Ala Glu Leu Gly Thr Ile Ala Gly Ser Glu
    130                 135                 140

Asp Gly Ile Val Asn Ser Glu Val Ile Tyr Ala Asp Pro Gln Glu Cys
145                 150                 155                 160

Tyr Thr Leu Val Thr Glu Thr Gln Val Asp Cys Leu Ala Ala Ala Leu
                165                 170                 175

Gly Ser Thr His Gly Leu Tyr Lys Gly Lys Ala Arg Leu Gly Phe Thr
            180                 185                 190

Glu Met Lys Ala Ile Ala Glu Gln Val Lys Val Pro Leu Val Leu His
        195                 200                 205
```

Gly Gly Thr Gly Ile Ala Asp Glu Asp Met Arg Arg Ala Ile Ala Cys
210             215                 220

Gly Thr Ala Lys Ile Asn Val Asn Thr Glu Asn Met Tyr Ala Trp Cys
225             230                 235                 240

Gln Gln Val Lys Ala Ile Phe Ala Ala Asp Thr Gly His Asp Val Asn
            245                 250                 255

Asp Pro Arg Lys Val Ile Ala Gln Gly Leu Gln Pro Val Arg Glu Met
            260                 265                 270

Ile Ala Arg Arg Met Ala Leu Phe Gly Ser Glu
            275                 280

<210> SEQ ID NO 6
<211> LENGTH: 364
<212> TYPE: PRT
<213> ORGANISM: Homo sapiens

<400> SEQUENCE: 6

Met Pro His Ser Tyr Pro Ala Leu Ser Ala Glu Gln Lys Lys Glu Leu
1               5                   10                  15

Ser Asp Ile Ala Leu Arg Ile Val Ala Pro Gly Lys Gly Ile Leu Ala
            20                  25                  30

Ala Asp Glu Ser Val Gly Ser Met Ala Lys Arg Leu Ser Gln Ile Gly
            35                  40                  45

Val Glu Asn Thr Glu Glu Asn Arg Arg Leu Tyr Arg Gln Val Leu Phe
50              55                  60

Ser Ala Asp Asp Arg Val Lys Lys Cys Ile Gly Gly Val Ile Phe Phe
65              70                  75                  80

His Glu Thr Leu Tyr Gln Lys Asp Asp Asn Gly Val Pro Phe Val Arg
            85                  90                  95

Thr Ile Gln Asp Lys Gly Ile Val Gly Ile Lys Val Asp Lys Gly
            100                 105                 110

Val Val Pro Leu Ala Gly Thr Asp Gly Glu Thr Thr Thr Gln Gly Leu
            115                 120                 125

Asp Gly Leu Ser Glu Arg Cys Ala Gln Tyr Lys Lys Asp Gly Ala Asp
130             135                 140

Phe Ala Lys Trp Arg Cys Val Leu Lys Ile Ser Glu Arg Thr Pro Ser
145             150                 155                 160

Ala Leu Ala Ile Leu Glu Asn Ala Asn Val Leu Ala Arg Tyr Ala Ser
            165                 170                 175

Ile Cys Gln Gln Asn Gly Ile Val Pro Ile Val Glu Pro Glu Ile Leu
            180                 185                 190

Pro Asp Gly Asp His Asp Leu Lys Arg Cys Gln Tyr Val Thr Glu Lys
            195                 200                 205

Val Leu Ala Ala Val Tyr Lys Ala Leu Ser Asp His His Val Tyr Leu
            210                 215                 220

Glu Gly Thr Leu Leu Lys Pro Asn Met Val Thr Pro Gly His Ala Cys
225             230                 235                 240

Pro Ile Lys Tyr Thr Pro Glu Glu Ile Ala Met Ala Thr Val Thr Ala
            245                 250                 255

Leu Arg Arg Thr Val Pro Pro Ala Val Pro Gly Val Thr Phe Leu Ser
            260                 265                 270

Gly Gly Gln Ser Glu Glu Glu Ala Ser Phe Asn Leu Asn Ala Ile Asn
            275                 280                 285

Arg Cys Pro Leu Pro Arg Pro Trp Ala Leu Thr Phe Ser Tyr Gly Arg
290             295                 300

-continued

```
Ala Leu Gln Ala Ser Ala Val Asn Ala Trp Arg Gly Gln Arg Asp Asn
305                 310                 315                 320

Ala Gly Ala Ala Thr Glu Glu Phe Ile Lys Arg Ala Glu Val Asn Gly
                325                 330                 335

Leu Ala Ala Gln Gly Lys Tyr Glu Gly Ser Gly Glu Asp Gly Gly Ala
            340                 345                 350

Ala Ala Gln Ser Leu Tyr Ile Ala Asn His Ala Tyr
        355                 360
```